(12) United States Patent
Snyder et al.

(10) Patent No.: US 7,463,922 B1
(45) Date of Patent: Dec. 9, 2008

(54) CIRCUIT AND METHOD FOR ANALYZING A PATIENT'S HEART FUNCTION USING OVERLAPPING ANALYSIS WINDOWS

(75) Inventors: David E Snyder, Bainbridge Island, WA (US); Thomas D Lyster, Bothell, WA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 1344 days.

(21) Appl. No.: 09/615,280

(22) Filed: Jul. 13, 2000

(51) Int. Cl.
*A61N 1/39* (2006.01)
(52) U.S. Cl. .......................................... 607/5
(58) Field of Classification Search ................. 607/2–5, 607/7, 9, 13, 6, 14
See application file for complete search history.

(56) References Cited

U.S. PATENT DOCUMENTS

| | | | |
|---|---|---|---|
| 4,919,144 A * | 4/1990 | Vandehey | 128/903 |
| 5,048,521 A * | 9/1991 | Pless et al. | 607/4 |
| 5,607,454 A | 3/1997 | Cameron et al. | |
| 5,735,879 A | 4/1998 | Gliner et al. | |
| 5,836,993 A | 11/1998 | Cole | |
| 5,879,374 A | 3/1999 | Powers et al. | |
| 5,987,356 A * | 11/1999 | DeGroot | 607/5 |
| 6,151,524 A * | 11/2000 | Krig et al. | 607/14 |
| 6,263,238 B1 * | 7/2001 | Brewer et al. | 607/5 |

* cited by examiner

*Primary Examiner*—George R Evanisko
(74) *Attorney, Agent, or Firm*—Tony Piotrowski

(57) ABSTRACT

A circuit includes a sensor coupled to a processor. The sensor senses an electrical signal that is representative of a patient parameter, and the processor determines a condition of the patient by analyzing first and second overlapping portions of the sensed electrical signal. For example, a portable AED can include such a circuit to sense first and second overlapping sections of an ECG. By utilizing this overlapping-window technique, the AED can obtain and analyze multiple sections of ECG data, and thus can make a shock/no-shock decision, more quickly than an AED using contiguous-window analysis. Thus, the overlapping-window technique allows one to use both longer ECG sections (better accuracy per window) and more of these longer sections (better voting accuracy) over a given analysis time. Furthermore, this overlapping-window technique significantly reduces or eliminates boundary problems because the boundary of one ECG section is within the interior of either the preceding or the following overlapping ECG section.

9 Claims, 11 Drawing Sheets

CIRCUIT AND METHOD FOR ANALYZING A PATIENT'S HEART FUNCTION USING OVERLAPPING ANALYSIS WINDOWS

TECHNICAL FIELD

The invention relates generally to electronic circuits and systems, and more particularly to a circuit and method for analyzing a patient's heart function using overlapping analysis windows. For example, a portable automatic external defibrillator (AED) can analyze overlapping portions of an electrocardiogram (ECG) to determine if a patient's heart would benefit from a defibrillating shock. By analyzing overlapping portions of the patient's ECG, the AED often makes a shock/no-shock decision more quickly and more accurately than AEDs using other analysis techniques.

BACKGROUND OF THE INVENTION

Portable AEDs have saved many lives in non-hospital settings and, as a result of advances in AED technology, the number of lives saved per year is rising. Typically, a portable AED analyzes a patient's heart function and instructs an operator to administer an electrical shock if appropriate. For example, a shock can often revive a patient who is experiencing ventricular fibrillation (VF). Because older models of portable AEDs include only basic diagnostic and safety features, they are often difficult to operate. Therefore, only specially trained persons such as emergency medical technicians (EMTs) can use these older models to administer shocks. Newer models, however, often include advanced diagnostic and safety features that allow minimally trained persons to administer shocks. Consequently, more people are using portable AEDs to save lives.

Because a heart condition that responds to an electrical shock can cause permanent damage or death within a short time if left untreated, a portable AED should be able to diagnose a shockable heart condition and be ready to shock a patient within seconds. Without cardiopulmonary resuscitation (CPR), a person in cardiac arrest will typically suffer permanent anoxia-induced brain damage within 4-6 minutes from the onset. Unfortunately, many people do not know how to administer CPR. And, even in the best of circumstances, it can take 1-4 minutes to retrieve the AED and 1-2 additional minutes to attach the pads to the patient, connect the pads to the AED, and activate the AED. Therefore, even if the patient is discovered immediately, the AED often has less than a minute to diagnose and shock the patient before he/she is in danger of suffering permanent brain damage. Clearly, the faster the AED can diagnose and shock the patient, the better the chances that the patient will survive with no permanent brain damage.

Unfortunately, many portable AEDs implement heart-analysis techniques that require a relatively long time to analyze the patient's ECG and to make a shock/no-shock decision based on the analysis.

FIGS. 1 and 2 illustrate contiguous windowing, which is a heart-analysis technique used by many portable AEDs. For example, referring to FIG. 1, a portable AED (not shown in FIG. 1) samples and analyzes contiguous "windows", i.e., sections 10a-10f, of a patient's ECG. Typically, the AED individually analyzes multiple ECG sections 10, compares the respective analysis results to one another or to predetermined comparison values, and makes a shock/no-shock decision based on this comparison.

Referring to FIG. 1, an AED (not shown in FIG. 1) using contiguous windowing often requires a relatively long time to make a shock/no-shock decision. For example purposes, assume that the AED is programmed to analyze at least ten ECG sections 10 before making a decision, and that each section 10 is two seconds long. Therefore, the AED requires a minimum of twenty seconds to make a shock/no shock decision. Even though twenty seconds may not seem like a long time, every second required to make a shock/no-shock decision decreases the chances that a patient will survive with no permanent damage.

In addition, changes in the patient's heart function may increase the time that the AED requires to make a shock/no-shock decision. For example purposes, assume that before the AED can make a shock/no-shock decision, it is programmed to analyze ECG sections 10 until at least a predetermined number of ten sequential sections give consistent analysis results. The AED then bases its shock/no-shock decision on one or more of these consistent analysis results. This decision-making process is often called "voting". The theory behind voting is that if a predetermined percentage of analyzed ECG sections yield consistent, i.e., similar results, then these results are more likely to be accurate than inconsistent results yielded by other ECG sections. For example, an AED may be programmed to accept the result yielded by the majority of analyzed ECG sections and ignore different results from the minority of analyzed ECG sections. In the illustrated example, the ECG section 10a indicates that the patient's heart is beating with a normal sinus rhythm, but the sections 10b-10f indicate that the patient is in VF. Therefore, because the analysis results obtained from the ECG section 10a will clearly be inconsistent with the results obtained from the sections 10b-10f, the AED must analyze at least seven ECG sections—the inconsistent section 10a plus at least six (a majority of ten) consistent sections starting with the section 10b—before making a shock/no-shock decision. If the six ECG sections starting with the section 10b are inconsistent, however, then the AED must analyze more ECG sections 10. Thus, the AED requires a minimum of fourteen seconds to make a shock/no-shock decision in this situation. Furthermore, although in this example the transition from normal sinus rhythm to VF occurs near the boundary between the ECG sections 10a and 10b, the same problem often arises when the transition occurs within a section 10.

Still referring to FIG. 1, one way to reduce the time that an AED requires to make a shock/no-shock decision is to shorten each of the ECG sections 10. For example, assuming that the AED is programmed to analyze at least ten sections 10 as discussed above, reducing the length of each section 10 from two seconds to one second reduces the minimum decision time from twenty to ten seconds. As the lengths of the ECG sections 10 decrease, the chances of an AED making an incorrect shock/no-shock decision increases. Specifically, as their lengths decrease, each of the sections 10 represents a smaller portion of the ECG. If a section 10 is too small, it does not contain enough ECG information to support an accurate analysis of the section. If all the sections 10 are too small, the AED makes a series of inaccurate analyses that may cause the AED to make an inaccurate shock/no-shock decision.

Another way to view this problem is as a tradeoff between section length and the number of sections. For example, for a given analysis time, e.g., 20 seconds, one can use longer sections (better accuracy per section) with fewer results to vote from (less voting accuracy) or shorter sections (less accuracy per section) with more results to vote from (more voting accuracy).

In addition, referring to FIG. 2, even when the ECG sections are not too short, an AED (not shown in FIG. 2) using contiguous windowing may incorrectly diagnose a patient's heart condition, and thus may determine that a defibrillating shock will benefit a patient when in actuality the shock may harm the patient. In the illustrated example, the patient is experiencing bradycardia, which is characterized by abnormalities in the patient's QRS wave and by an abnormally low heart rate. Unfortunately, shocking a patient experiencing bradycardia is at best useless and at worst can send the patient into VF or cause other cardiac damage. Therefore, it is important that the AED recognize bradycardia and other unshockable heart conditions and generate a no-shock decision if it determines that a patient is experiencing any of these conditions.

More specifically, if a boundary, i.e., the beginning or end, of an ECG section 12 intersects an important part of the ECG, then the AED's analysis of that section may yield an incorrect diagnosis, and the AED may make an incorrect shock/no-shock decision based on this incorrect diagnosis. In the illustrated example, the AED analyzes contiguous ECG sections 12a, 12b, 12c, which are each one and a half seconds long. Unfortunately, the beginning of the section 12a intersects a QRS complex, and thus the section 12a contains only part of the complex. Because there are no other full complexes within the section 12a, the AED's analysis of the section 12a may yield an incorrect result. But if the ECG sections 12b and 12c and a predetermined number of following sections 12 respectively include full QRS complexes, the AED can use voting to ignore the result from the section 12a and correctly make a no-shock decision as discussed above. Although as discussed above this may increase the time that the AED requires to make a shock/no-shock decision, the AED makes a correct decision. Conversely, if the ECG sections are shortened, e.g., to 0.5 seconds in order to obtain a quicker response, a majority of the sections will be lacking a QRS complex. These sections may be incorrectly interpreted as benefiting from a shock, resulting in an inappropriate shock diagnosis.

Still referring to FIG. 2, there are currently no analysis techniques for overcoming the intersecting-boundary problem other than to vote among multiple contiguous ECG sections, thereby delaying diagnosis, or to have a skilled operator (not shown in FIG. 2) study the ECG and determine if the AED's shock/no-shock decision is correct.

Therefore, the need has arisen for a heart-condition analysis technique that is faster and more accurate than the contiguous-window analysis technique.

SUMMARY OF THE INVENTION

In one aspect of the invention, a circuit includes a sensor coupled to a processor. The sensor senses an electrical signal that is representative of activity in a patient's heart, and the processor determines a condition of the patient's heart by analyzing first and second overlapping portions of the sensed electrical signal.

For example, a portable AED can include such a circuit to sense a first section of an ECG during a first time period and to sense a second section of the ECG during a second time period that overlaps the first time period. By utilizing this overlapping-window technique, the AED can obtain and analyze multiple sections of ECG data, and thus can make a shock/no-shock decision, more quickly than an AED using contiguous-window analysis. Thus, the overlapping-window technique allows one to use both longer ECG sections (better accuracy per window) and more of these longer sections (better voting accuracy) over a given analysis time. Furthermore, this overlapping-window technique significantly reduces or eliminates boundary problems because the boundary of one ECG section is within the interior of one or more of the either the preceding or the following overlapping ECG sections.

DESCRIPTION OF THE INVENTION

Figure 3A:
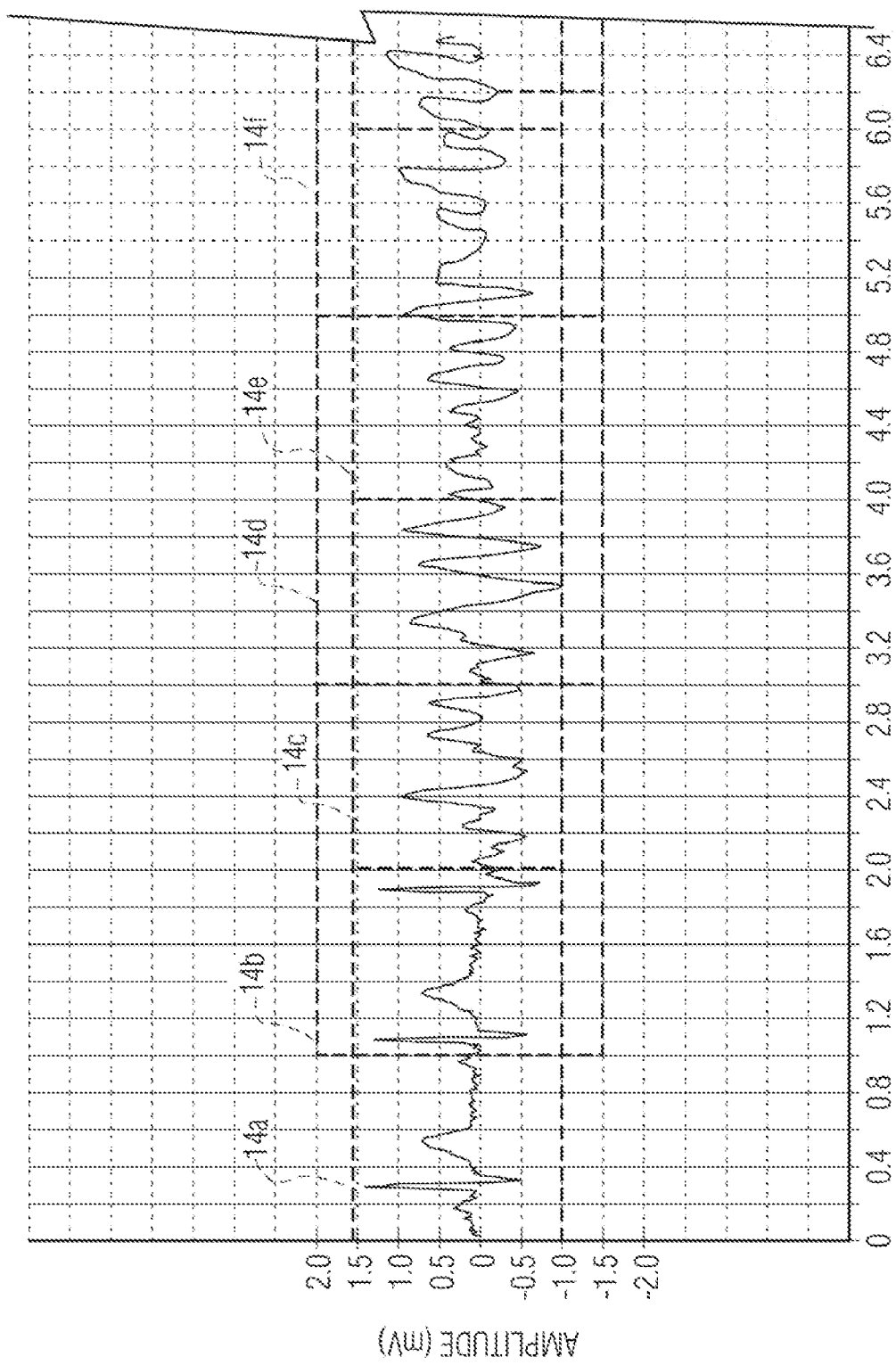
FIG. 3 illustrates an overlapping-window analysis of a portion of the ECG of FIG. 1 according to an embodiment of the invention.
Figure 3B:
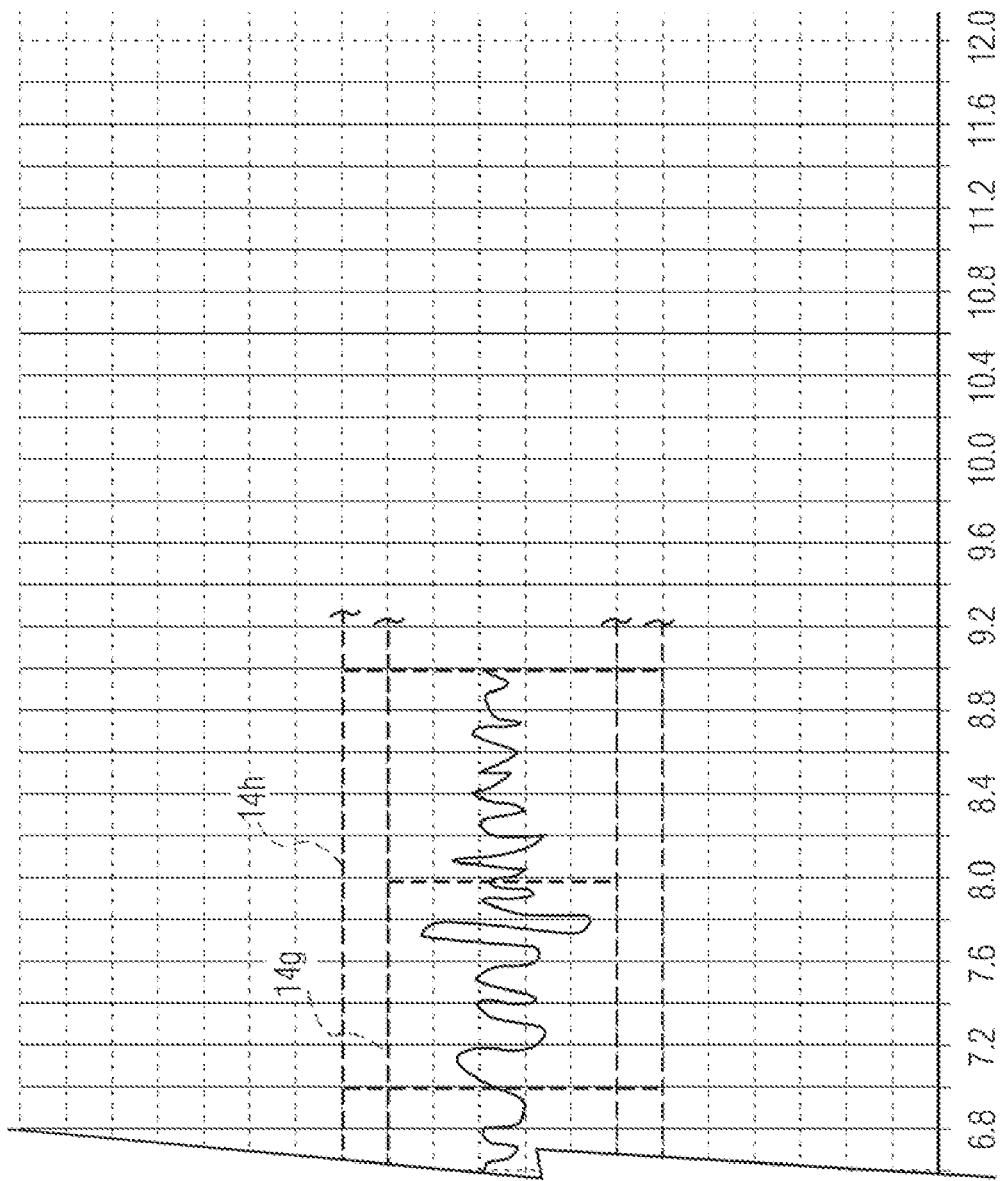
Figure 4:
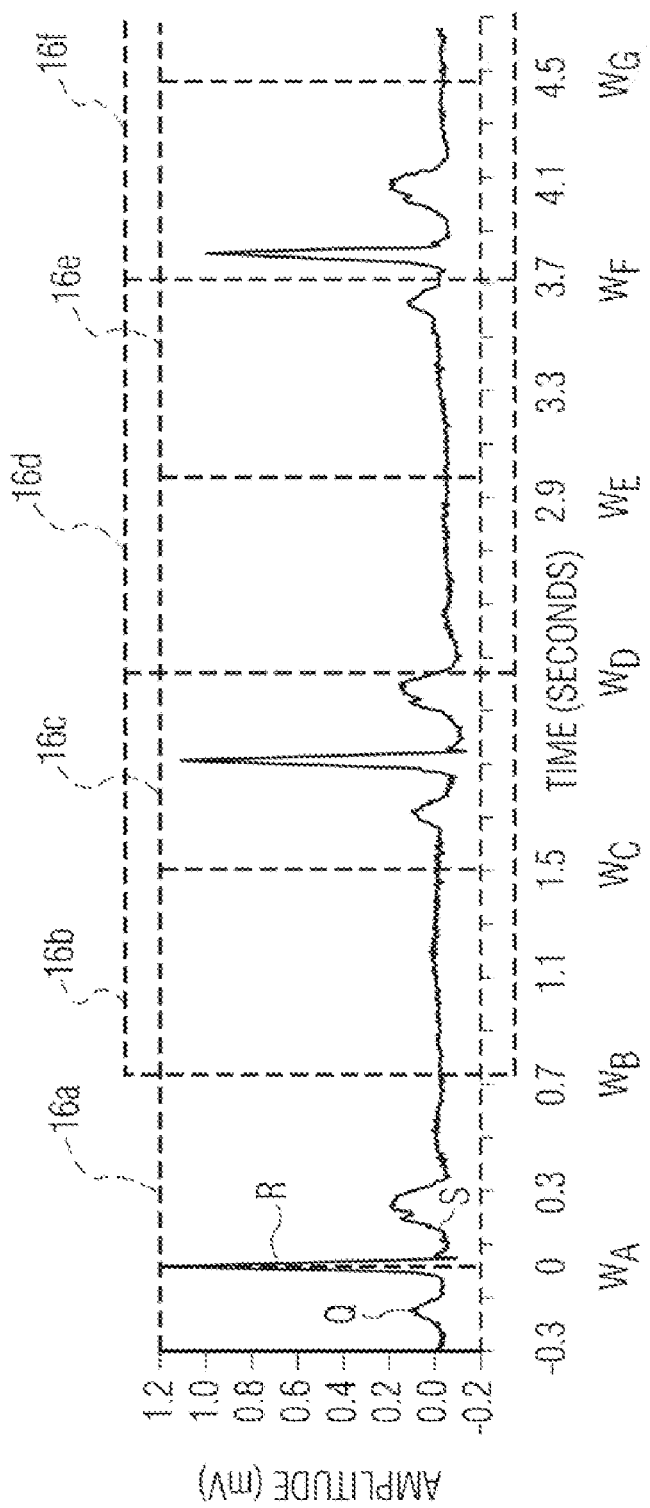
FIG. 4 illustrates an overlapping-window analysis of the ECG of FIG. 2 according to an embodiment of the invention.

FIGS. 3 and 4 illustrate overlapping-window analysis of an ECG according to respective embodiments of the invention. As discussed below, an AED using overlapping-window analysis often can diagnose a patient's heart condition more quickly and more accurately than an AED using contiguous-window analysis. Furthermore, an AED using overlapping-window analysis is often more immune to boundary problems than an AED using contiguous-window analysis. Moreover, although overlapping-window analysis is described below in terms of a portable AED analyzing an ECG, other types of medical equipment can use this technique to analyze other types of signals, such as an electrogram that represent a patient's heart activity, or an electroencephalogram that represents a patient's brain activity.

Figure 1A:
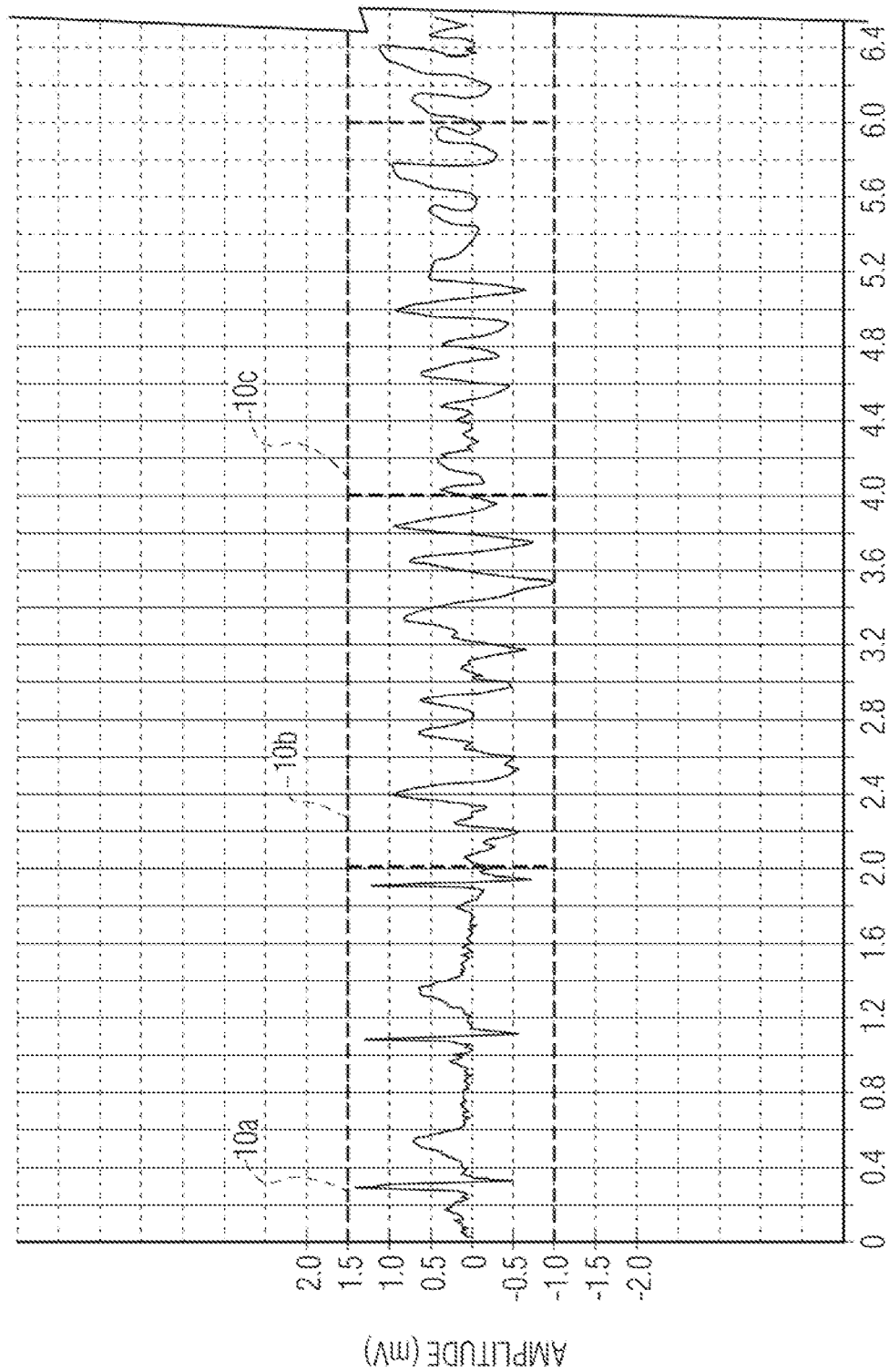
FIG. 1 illustrates a conventional contiguous-window analysis of the ECG of a patient who suddenly enters VF.
Figure 1B:
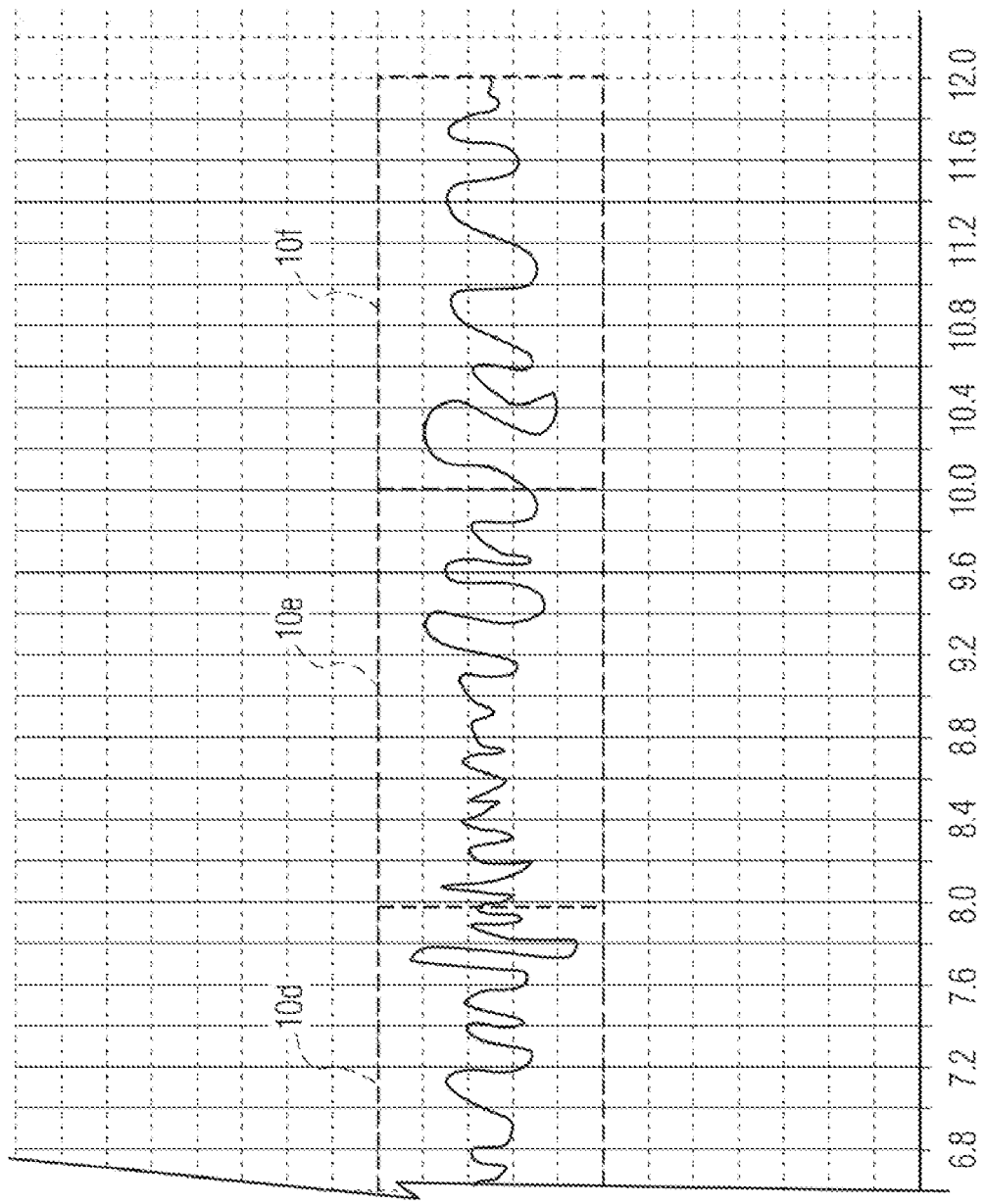

FIG. 3 illustrates an overlapping-window analysis of a portion of the ECG of FIG. 1 according to an embodiment of the invention. Like the contiguous ECG sections 10 of FIG. 1, each section 14 is two seconds long, although in other embodiments the sections 14 may be longer or shorter than two seconds or may not all have the same length. But unlike the sections 10, the sections 14 overlap one another. For example, the beginning of the second section 14b coincides with the midpoint of the first section 14a, and the end of the section 14b coincides with the midpoint of the third section 14b. Thus, the first half of each ECG section 14 overlaps the last half of the respective preceding section, and the last half of each ECG section 14 overlaps the first half of the respective following section. This is referred to as 50% overlap, although in other embodiments the overlap can be greater or less than 50%. Therefore, overlapping-window analysis allows an AED circuit (not shown in FIG. 3) to analyze overlapping sections of an ECG or other heart signal. Because the AED can use conventional algorithms to analyze each of the overlapping ECG sections, a detailed discussion of these algorithms is omitted.

By analyzing overlapping sections of a patient's ECG, an AED can often make a shock/no-shock decision more quickly than it can by analyzing contiguous ECG sections. Specifically, because the ECG sections 14 overlap one another, the AED can analyze more sections 14 of the ECG within a given time period than it can contiguous sections 10 (FIG. 1). For example, the AED can analyze ten overlapping sections 14 in eleven seconds as compared to analyzing ten contiguous sections 10 in twenty seconds. Thus, 50% overlapping cuts the analysis time almost in half!

Furthermore, analyzing overlapping sections of a patient's ECG is often more accurate than analyzing contiguous sections of the ECG. As discussed above in conjunction with FIGS. 1 and 2, if an ECG section is too small, it often contains too little information to yield an accurate indication of the patient's heart condition. Therefore, analyzing a number of longer, overlapping ECG sections of an ECG segment is often more accurate than analyzing a similar number of shorter, contiguous ECG sections of the same segment. For example, analyzing an eleven-second ECG segment with ten overlapping two-second sections 14 is often more accurate than analyzing the ECG segment with eleven contiguous one-second ECG sections. Because a section 14 is twice as long as a one-second section, it contains approximately twice as much information as the one-second section. Therefore, the longer sections 14 each provide a "bigger picture" of the patient's ECG than do the shorter contiguous sections, and thus tend to yield a more accurate indication of the patient's heart condition.

Moreover, by analyzing overlapping sections of a patient's ECG, an AED can often detect changes in a patient's heart condition more quickly than by analyzing contiguous sections. For example, assume that before an AED can make a shock/no-shock decision, it is programmed to analyze ECG sections until a majority of five sequential sections gives consistent analysis results. Referring to FIG. 1, because the ECG does not indicate VF until the beginning of the section 10b, an AED using contiguous windowing must analyze at least four ECG sections 10a-10d, and thus requires at least eight seconds to determine that the patient is in VF. Conversely, referring to FIG. 3, an AED using the illustrated overlapping-windowing technique may be able to diagnose VF in as few as six seconds. Specifically, because the ECG does not indicate VF until the middle of the section 14b, an AED using the illustrated overlapping-windowing technique analyzes at least five ECG sections 14a-14e. But because the sections 14 overlap one another by 50%, five ECG sections 14 occupy a shorter period of time (six seconds) than four of the contiguous ECG sections 10 (eight seconds) of FIG. 1. Of course, increasing the overlap or decreasing the length of the sections 14 may further reduce the minimum analysis time.

Figure 2:
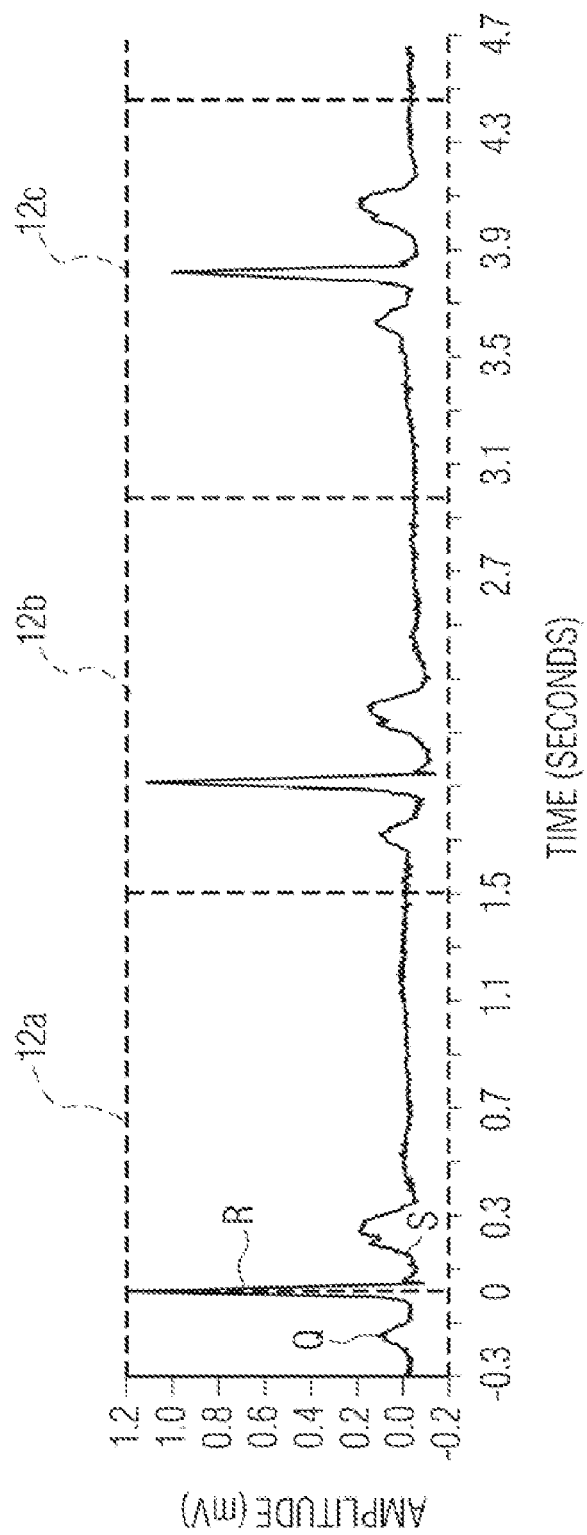
FIG. 2 illustrates a conventional contiguous-window analysis of the ECG of a patient experiencing bradycardia.

FIG. 4 illustrates an overlapping-window analysis of the ECG of FIG. 2 according to an embodiment of the invention. Like the ECG sections 12 of FIG. 2, the ECG sections 16a-16f are each 1.5 seconds long, although in other embodiments the sections 16 may be longer or shorter. But unlike the sections 12, the sections 16 overlap one another by 50%, although in other embodiments the sections 16 may overlap one another by more or less than 50%. Therefore, the beginning of a section 16 is within the preceding section and the end of the section 16 is within the following section. For example, the beginning of the second section 16b at time $W_B$ coincides with the midpoint of the first section 16a, and the end of the section 16b at time $W_D$ coincides with the midpoint of the third section 16c. Thus, if an important part of the ECG intersects the boundary of a section 16, this ECG part is most often wholly within another section 16. Therefore, an AED can analyze ECG sections 16 that wholly contain important parts of the ECG. For example, if the QRS complexes of the ECG were to intersect with the boundaries of the sections 16a, 16c, and 16e at the respective times $W_A$, $W_C$, and $W_E$, then these same QRS complexes also intersect the midpoints of the alternate sections 16b, 16d, and 16f. Therefore, by analyzing the alternate sections 16b, 16d, 16f, and so on, the AED can analyze whole QRS complexes and thus correctly diagnose bradycardia and make a no-shock decision.

Figure 5:
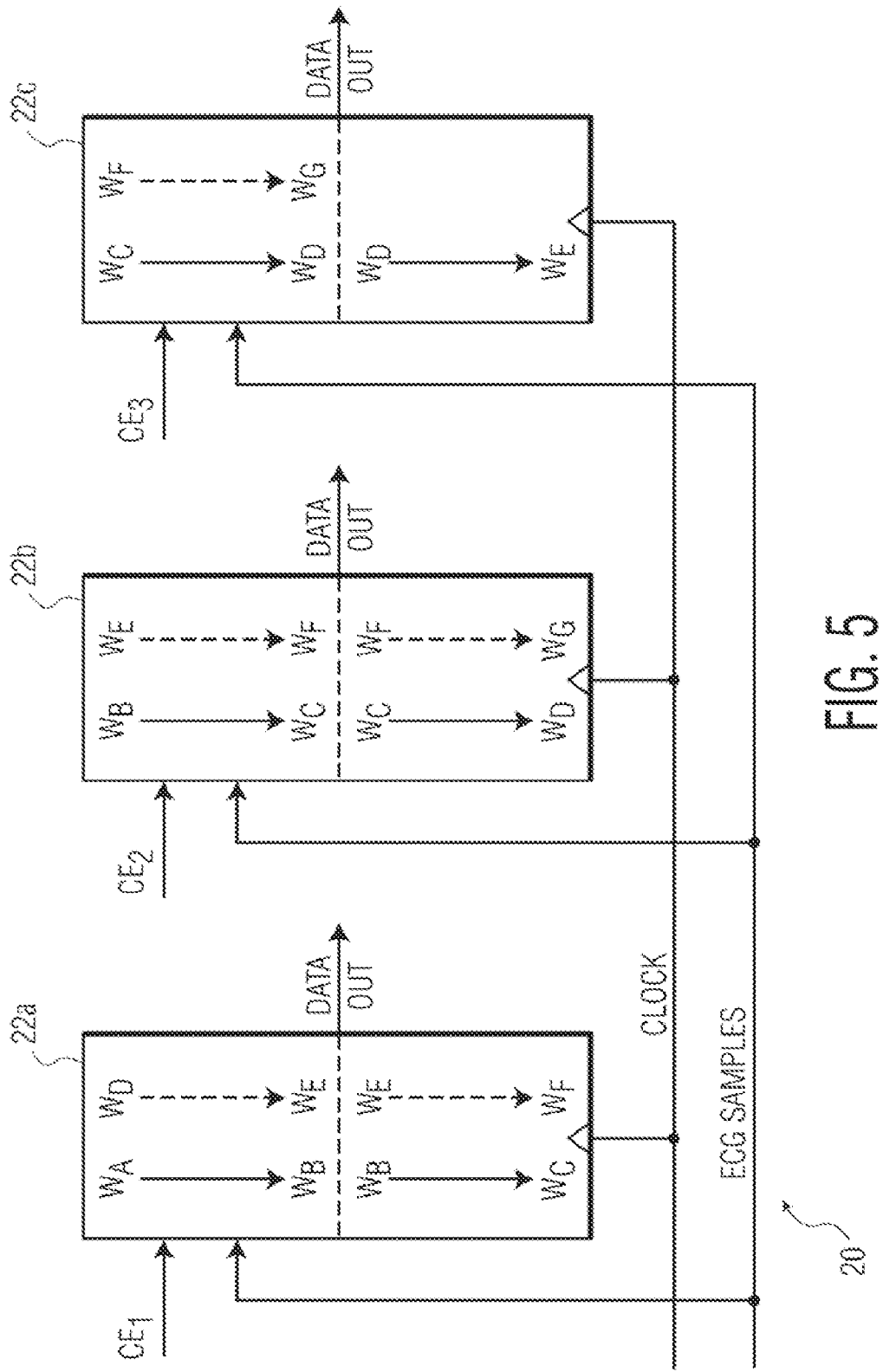
FIG. 5 is a block diagram of a memory circuit for storing overlapping sections of an ECG according to an embodiment of the invention.

FIG. 5 is a block diagram of a memory circuit 20 that can store overlapping sections of an ECG according to an embodiment of the invention. The memory circuit 20 includes three memories 22a, 22b, and 22c, which may be disposed within a common memory array or within respective memory arrays. Each of the memories 22a, 22b, and 22c stores data representing a respective overlapping ECG section in response to a common signal CLOCK and respective memory-enable signals CE1, CE2, and CE3. For example, referring to FIG. 4 and as discussed below, at various points during the ECG analysis, the memory 22a stores data representing the ECG section 16a, the memory 22b stores data representing the section 16b, and the memory 22c stores data representing the section 16c. In one embodiment, the stored data are conventional analog or digital samples—typically voltage samples—of the ECG. Once the data representing an ECG section is stored in a memory 22, the AED (not shown in FIG. 5) can analyze the overlapping ECG section stored within that memory 22. As discussed below, once the AED analyzes the stored data, the memory 22 begins to store another ECG section. Therefore, for 50% overlap, the three memories 22a, 22b, and 22c can sequentially store data for all of the overlapping ECG sections regardless of how many sections the AED analyzes. But more or fewer memories 22 may be needed for different amounts of overlap.

Figure 6:
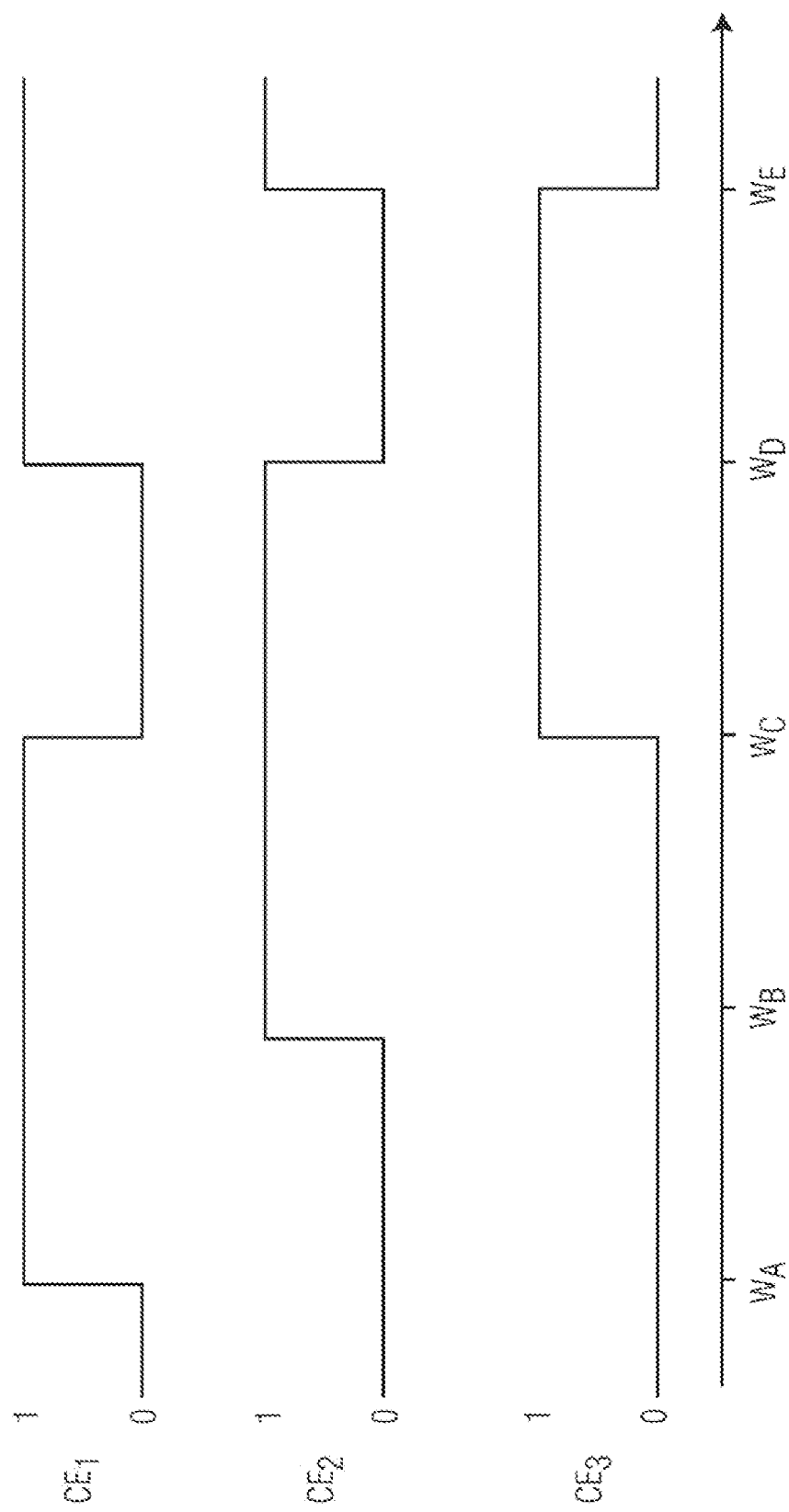
FIG. 6 is a timing diagram of some of the signals shown in FIG. 5.

Referring to FIGS. 4-6, the operation of the memory circuit 20 is discussed according to an embodiment of the invention. FIG. 6 is a timing diagram of the signals CE1, CE2, and CE3 of FIG. 5, where the times $W_A$-$W_E$ respectively correspond to the same times $W_A$-$W_E$ in FIG. 4, and where CE1, CE2, and CE3 are active logic 1 and inactive logic 0.

Before time $W_A$, CE1, CE2, and CE3 are inactive logic 0 such that the memories 22a-22c are disabled from storing samples of the ECG.

Next, between times $W_A$ and $W_B$, the memory 22a stores data representing the first half of the ECG section 16a. Specifically, a sample circuit (not shown in FIGS. 4-6) generates a stream of ECG samples, which are coupled to the memories 22a-22c. At time $W_A$, CE1 transitions to an active logic 1, and thus enables the memory 22a to begin storing the ECG samples that represent the ECG section 16a. Therefore, at time $W_B$, the memory has stored samples that represent the first half of the section 16a. To clearly illustrate this, FIG. 5 shows that half the memory 22a is filled between the times $W_A$ and $W_B$, thus indicating that the memory 22a has just enough capacity to store the ECG samples representing the section 16a. In other embodiments, however, the memories 22a-22c may have larger capacities.

Then, between the times $W_B$ and $W_C$, the memory 22a stores data representing the second half of the ECG section 16a, and the memory 22c stores data representing the first half of the ECG section 16b. Specifically, at time $W_B$, the signal CE2 transitions to an active logic 1, and thus enables the memory 22b to begin storing the ECG samples that represent the second ECG section 16b. Furthermore, the memory 22a begins storing the same samples, which also represent the second half of the ECG section 16a. Thus, by storing the same portion of the ECG—the overlapping portion between times $W_B$ and $W_C$—in two memories 22a and 22b, the memory circuit 20 stores overlapping ECG sections 16a and 16b.

Next, between the times $W_C$ and $W_D$, the AED analyzes the data stored in the memory 22a, the memory 22b stores data representing the second half of the ECG section 16b, and the memory 22c stores data representing the first half of the ECG section 16c. Specifically, at time $W_C$, CE3 transitions to active logic 1 and CE1 transitions to inactive logic 0. Furthermore, the memory 22a contains ECG samples that represent the entire ECG section 16a, and the memory 22b contains ECG samples that represent the first half of the ECG section 16b. Between $W_C$ and $W_D$, the AED analyzes the data in the memory 22a, and thus analyzes the first ECG section 16a, while the memory 22b stores the second half of the ECG section 16b and the memory 22c stores the first half of the ECG section 16c. Therefore, while the AED analyzes data in one memory 22, the other two memories 22 continue to store ECG samples.

Then, between the times $W_D$ and $W_E$, the AED analyzes the data stored in the memory 22b, the memory 22a stores data representing the first half of the ECG section 16d, and the memory 22c stores data representing the second half of the ECG section 16c. Specifically, at time $W_D$, CE1 transitions to active logic 1 and CE2 transitions to inactive logic 0. Furthermore, the memory 22b contains ECG samples that represent the entire ECG section 16b, and the memory 22c contains ECG samples that represent the first half of the ECG section 16c. Between $W_D$ and $W_E$, the AED analyzes the data in the memory 22b, and thus analyzes the second ECG section 16b, while the memory 22c stores the second half of the section 16c and the memory 22a stores the first half of the section 16d.

This cycle of storing and analyzing data continues until the AED analyzes the desired number of overlapping ECG sections 16.

Referring to FIG. 5, other embodiments of the memory circuit 20 are discussed. For example, although described as storing ECG sections having a 50% overlap, the memory 20 for storing ECG sections can be modified to have a smaller or larger overlap. Furthermore, although they are described as storing the same ECG samples for the overlapping portion of two ECG sections, the memories 22a-22c may store different samples for the same overlapping portion. For example, as discussed above, between the times $W_B$ and $W_C$ the memories 22a and 22b store the same ECG samples for the second half of the ECG section 16a and the first half of the ECG section 16b, respectively.

Moreover, as discussed below in conjunction with FIG. 7, other circuits can be used or designed, such as a linear register to store overlapping portions of a patient's ECG.

Figure 7:
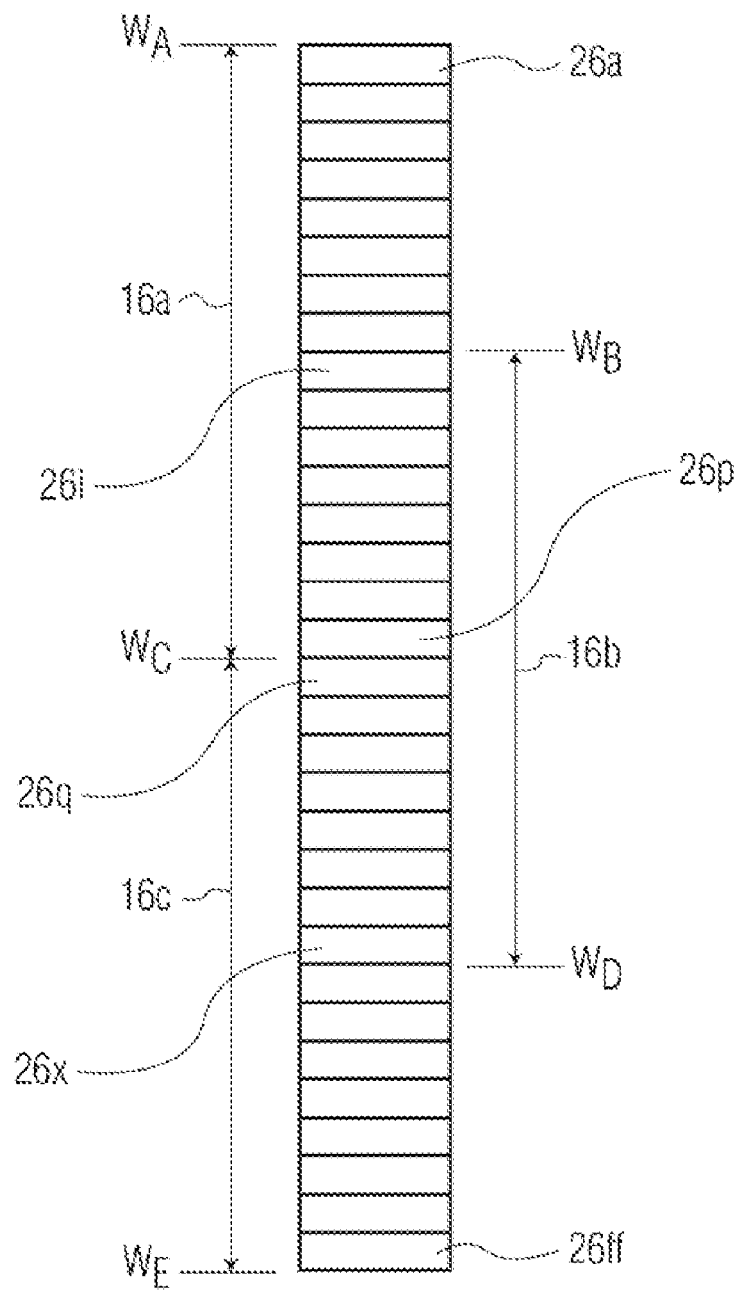
FIG. 7 is a block diagram of a memory circuit for storing overlapping sections of an ECG according to another embodiment of the invention.

FIG. 7 is a block diagram of a linear memory circuit 24 that can store overlapping sections of an ECG according to another embodiment of the invention. Specifically, the memory circuit 24 is more efficient than the memory circuit 20 of FIG. 5 because it can store the same number of contiguous ECG sections as the memory circuit 20 with fewer storage locations.

The memory circuit 24 includes a number of storage locations 26, which each store a sample of the patient's ECG. Assuming for example purposes that each window 16 (FIG. 4) is sixteen samples long, initially the circuit 24 stores the ECG section 16a in locations 26a-26p, section 16b in locations 26i-26x, and section 16c in locations 26q-26ff. Therefore, in this example, the memory circuit 20 (FIG. 5) requires forty eight storage locations to store three windows 16, but the memory circuit 24 requires only thirty two storage locations 26 to store three windows 16.

Referring to FIGS. 4 and 7, in operation, between times $W_A$-$W_E$, the memory circuit 24 sequentially stores the ECG samples for the ECG sections 16a-16c starting at the location 26a and ending at the location 26ff. Once an entire section 16 stored, the AED analyzes it while the circuit 24 finishes storing the remaining samples of the next section 16. Similarly, between times $W_E$-$W_I$ ($W_H$ and $W_I$ omitted from FIG. 4 for clarity), the circuit 24 stores the ECG samples for the next three windows 16d-16f by sequentially overwriting the locations 26a-26ff. The circuit 24 repeats this process until AED stores and analyzes the desired number of ECG sections 16.

Still referring to FIG. 7, although the memory circuit 24 is described as being large enough to store three overlapping ECG sections 16, in other embodiments the circuit 24 may be able to store more or fewer sections 16.

Figure 8:
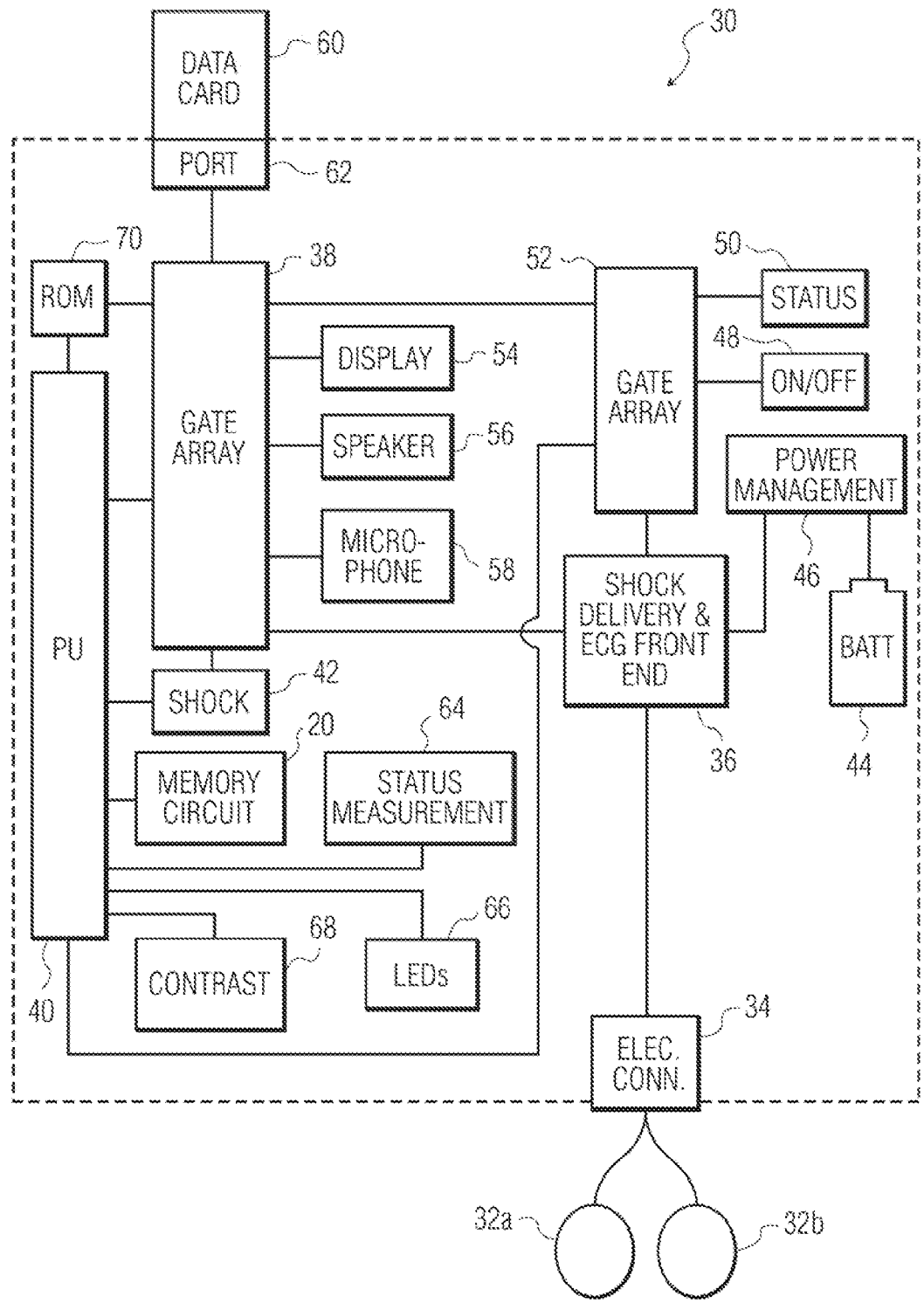
FIG. 8 is a block diagram of an AED circuit that implements an overlapping-window analysis according to an embodiment of the invention.

FIG. 8 is a block diagram of an AED circuit 30, which analyzes overlapping sections of a patient's ECG (not shown in FIG. 8) according to an embodiment of the invention. In the described embodiment, the circuit 30 includes the memory circuit 20 of FIG. 5, although in other embodiments the circuit 30 may analyze overlapping ECG sections using the memory circuit 24 of FIG. 7 or another ECG-storage circuit.

Referring to FIG. 8, conventional defibrillator pads 32a and 32b are coupled to the circuit 30 via a conventional connector 34 and are operable to sense a patient's ECG and to apply an electrical shock to the patient. A shock-delivery-and-ECG front-end circuit 36 samples the patient's ECG during an analysis mode of operation and provides a shock to the patient via the connector 34 and pads 32a and 32b during a shock-delivery mode of operation. A gate array 38 receives the ECG samples from the circuit 36 and provides them to a processor unit (PU) 40, which stores the samples in the memory circuit 20 and analyzes the overlapping ECG sections that the stored samples represent as discussed above in conjunction with FIGS. 4-6. Although the memory circuit 20 is shown coupled directly to the processor unit 40, the circuit 20 may actually be part of the processor unit 40 or be coupled to the processor unit 40 through other circuits such as the gate array 38. If the analysis of the overlapping ECG sections indicates that the patient is suffering from a shockable heart condition, then the processor unit 40 instructs the circuit 36 via the gate array 38 to enable delivery of a shock when an operator (not shown in FIG. 8) presses a shock button 42. Conversely, if the analysis of the overlapping ECG sections indicates that the patient is not suffering from a shockable heart condition, then the processor unit 40 disables the shock delivery circuitry 36 from delivering a shock to the patient.

Still referring to FIG. 8, the circuit 30 includes a power-management circuit 46 for distributing power from a battery 44 to the subcircuits of the circuit 30. An on/off switch 48 turns the circuit 30 on and off, a status circuit 50 indicates the status of the circuit 30, and a gate array 52 interfaces the power-management circuit 46, the on/off circuit 48, and the status circuit 50 to the circuit 36, the processor unit 40, and the gate array 38. A display 54 displays information to an operator (not shown in FIG. 7), a speaker 56 provides audio instructions to the operator, and a microphone 58 records the operator's voice and other audible sounds. A data card 60 is connected to the gate array 38 via a port 62. The card 60 stores the operator's voice and other audible sounds along with the patient's ECG and a record of AED events for later study. A status-measurement circuit 64 provides the status of the circuit 30 subcircuits to the processor unit 40, and LEDs 66 provide information to the operator such as whether the processor unit 40 has enabled the circuit 36 to deliver a shock to the patient. A contrast button 68 allows the operator to control the contrast of the display screen 54, and a memory such as a read only memory (ROM) 70 stores programming information for the processor unit 40 and the gate arrays 38 and 52.

The AED circuit 30 and other AED circuits are further discussed in the following references, which are incorporated by reference: U.S. Pat. No. 5,836,993; U.S. Pat. Nos. 5,735,879, ELECTROTHERAPY METHOD AND APPARATUS, filed Aug. 6, 1993; 5,607,454, ELECTROTHERAPY METHOD AND APPARATUS, filed Apr. 14, 1994; and, 5,879,374, DEFIBRILLATOR WITH SELF-TEST FEATURES, filed May 10, 1994.

Figure 9:
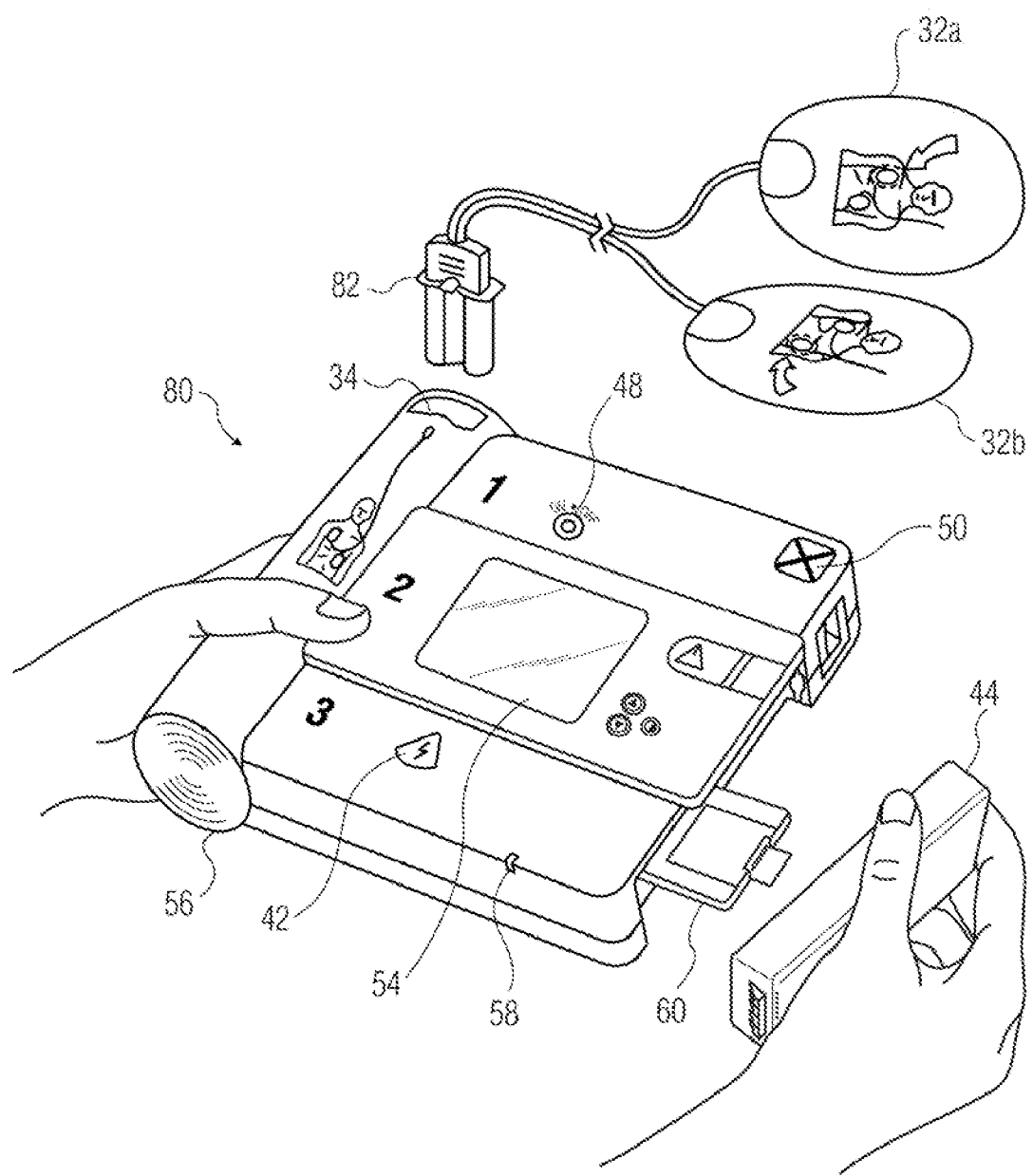
FIG. 9 is a perspective view of a portable AED that incorporates the AED circuit of FIG. 8 according to an embodiment of the invention.

FIG. 9 is a perspective view of a portable AED 80, which incorporates the circuit 30 of FIG. 8 according to an embodiment of the invention. For clarity, common elements in FIGS. 8 and 9 are referenced with like numerals.

During an emergency where it is determined that a patient (not shown in FIG. 9) may need a shock, an operator (hands shown in FIG. 9) retrieves the AED 80 and installs the battery 44 if it is not already installed. Next, the operator removes the pads 32a and 32b from a protective package (not shown in FIG. 9) and inserts a pad connector 82 into the connector 32. Then, the operator turns the on/off switch 48, which is a key switch in this embodiment, to the "on" position to activate the AED 80. Following the instructions displayed on the display 54 or "spoken" via the speaker 56, the operator places the pads 32a and 32b on the patient in the respective positions shown in the pictures on the pads and on the AED 80. After the operator places the pads 32a and 32b on the patient, the processor unit 40 (FIG. 8) analyzes the patient's ECG to determine whether the patient is suffering from a shockable heart condition. If the processor unit 40 determines that the patient is suffering from a shockable heart condition, then the display 54 or the speaker 56 instructs the operator to depress the shock button 42 to deliver a shock to the patient. Conversely, if the processor unit 40 determines that the patient is not suffering from a shockable heart condition, the display 54 or the speaker 56 informs the operator to seek appropriate non-shock treatment for the patient. Furthermore, the processor unit 40 disables the shock-delivery circuit 36 such that even if the operator presses the shock button 42, the circuit AED 80 does not shock the patient.

As discussed above in conjunction with FIG. 8, the microphone 58 may record the voice of the operator and of other rescuers and, the data card 60 may store these voices and the patient's ECG for later study. Such study may be for the purposes of instructing others in rescue techniques, for evaluating the performances of the operator or other rescuers, or for improving the AED 80.

From the foregoing it will be appreciated that, although specific embodiments of the invention have been described herein for purposes of illustration, various modifications may be made without deviating from the spirit and scope of the invention.

What is claimed:

1. An external defibrillator which analyzes an ECG signal for an indication of ventricular fibrillation (VF), comprising:
   a sensor operable to sense an ECG segment; and
   a processor unit coupled to the sensor and operable to analyze a plurality of ECG sections of the ECG segment for an indication of VF, each ECG section comprising digital samples of a continuous ECG heart waveform sensed during a window of time, wherein a window of one ECG waveform overlaps a portion of the window of at least one other ECG waveform and the processor is operable to analyze said window of the ECG waveform and said overlapping window of said ECG waveform to determine the indication of said VF; and
   a shock delivery circuit responsive to the indication of VF to deliver a shock.

2. The external defibrillator of claim 1, further comprising a memory coupled to the sensor and to the processor and operable to store the overlapping portions of the ECG sections.

3. The external defibrillator of claim 1 wherein the processor is operable to determine a shockable heart condition from the analysis of the ECG heart waveform of a plurality of overlapping ECG sections.

4. The external defibrillator of claim 1 wherein the processor is operable to determine from the analysis of the ECG heart waveform of a plurality of overlapping ECG sections that a patient is not suffering from a shockable heart condition.

5. The external defibrillator of claim 1, wherein a plurality of the ECG sections overlap the windows of two other ECG sections.

6. A method for using an external defibrillator to analyze an ECG segment for an indication of ventricular fibrillation (VF), comprising:
   sensing sections of digital samples of a continuous ECG heart waveform during a time interval, each of the sections comprising the ECG heart waveform of a period of time which overlaps the time period of another of the sections;
   analyzing the ECG heart waveform sensed during each of the sections to generate respective analysis results; and
   determining whether to deliver a shock to treat the VF based on the analysis results.

7. The method of claim 6 wherein the determining comprises determining from the analysis results whether shockable VF is or is not indicated.

8. The method of claim 7 wherein when the determining indicates shockable VF, enabling the external defibrillator to deliver a shock.

9. The method of claim 6, wherein a plurality of the sections each overlap the time periods of a previous section and a subsequent section.

* * * * *